US00PP25306P2

(12) United States Plant Patent
Odom

(10) Patent No.: US PP25,306 P2
(45) Date of Patent: Feb. 24, 2015

(54) ***RHODODENDRON INDICUM* PLANT NAMED 'JULONSO'**

(50) Latin Name: *Rhododendron indicum*
Varietal Denomination: Julonso

(71) Applicant: Richard G. Odom, Forest Hill, LA (US)

(72) Inventor: Richard G. Odom, Forest Hill, LA (US)

( * ) Notice: Subject to any disclaimer, the term of this patent is extended or adjusted under 35 U.S.C. 154(b) by 0 days.

(21) Appl. No.: 13/986,203

(22) Filed: Apr. 11, 2013

(51) Int. Cl.
*A01H 5/00* (2006.01)

(52) U.S. Cl.
USPC ..... Plt./240

(58) Field of Classification Search
CPC ..... A01H 5/00
USPC ..... Plt./240, 238
See application file for complete search history.

(56) References Cited

U.S. PATENT DOCUMENTS

PP14,343 P2 12/2003 Odom
PP14,360 P2 12/2003 Odom
PP14,362 P2 12/2003 Odom

*Primary Examiner* — June Hwu
*Assistant Examiner* — Keith Robinson
(74) *Attorney, Agent, or Firm* — Jones Walker, LLP

(57) ABSTRACT

A new and distinct variety of semi-dwarf azalea originated from a branch sport of 'Crimson Queen'. The new variety possesses a unique blush red foliage (185A-B, greyed-purple group), on new growth while the older leaves approximate N189-A & -B, Grayed-Green Group.

4 Drawing Sheets

Scientific name: *Rhododendron indicum.*

Cultivar or variety demonimation: 'Julonso'.

The plant belongs to a group of azaleas called the "Southern Indian azaleas" or "indicas" that are hybrids derived from various species of *Rhododendron* or derived directly from various species in that genus. *Rhododendron indicum* (L.) Sweet, although often given as the scientific name for this group of plants, has had little or no part in the parentage of the indicas. Most indicas are descendents of *Rhododendron simsii* Planch. *R. mucronatum* G. Don and/or *R. pulchrum* Sweet or their hybrids; in the industry, however, the accepted parentage is that of *Rhododendron indicum.*

BACKGROUND OF THE INVENTION

The present invention relates to a new and distinct variety of evergreen azaleas botanically known as *Rhododendron indicum*. Richard Odom discovered this new azalea variety in Forest Hill, La., hereinafter referred to as 'Julonso' as a naturally occurring branch sport of an Azalea 'Crimson Queen' (U.S. Plant Pat. No. 14,343), which is related to Azalea 'Red Formosa' an unpatented azalea that is well-known in the trade in zones 7-9. For comparison purposes, 'Crimson Queen' leaf characteristics are as follows: upper surface, greyed-purple group, 187-A, lower surface, greyed-purple group 184-B, while 'Red Formosa' characteristics are as follows: leaves upper surface, grayed-green group, N189A; leaves lower surface, green group, 138A; stem coloration 138-B Green group; bark coloration, 177-B Grayed-orange group; petiole coloration 138-B, 138-C Green Group.

Tip cuttings were taken from branches of 'Crimson Queen' that appeared to have a variation in coloring across the leaf surface. Cuttings were then taken from subsequent plants as they matured. All work was undertaken at a nursery in Forest Hill, La. After several generations of asexual propagation from rooting cuttings, the present plant has been developed with unique coloration and semi-dwarf growth habit.

Plant cuttings are allowed to root and grow in a 2.25 inch diameter (rosecup) container for 6-8 months, at which time the plant is about 3 inches in height, and is then transferred to a one gallon container. After an additional 10-12 months of growth, the plant is about 8-10 inches in height and about 8-10 inches in spread. At this time, the plant is sufficiently large for commercial sale as a one gallon plant. If larger plants are desired for commercial sale, the plant can be re-potted from the one gallon container to a three gallon container. An additional 8-10 months of growth in the three gallon container is generally needed to produce a commercial three gallon container plant, at about 18 inches in height and 20-22 inches in spread.

Asexual propagation of the new plant by rooting cuttings has been under Mr. Odom's direction in Forest Hill, La. Several generations of the new plant have been evaluated and the distinctive characteristics of the plant have remained stable. The plant cannot be reproduced true from seed.

SUMMARY OF THE INVENTION

'Julonso' a semi-dwarf indica azalea. Growth habit: Shape of the plant at maturity: Broad compact, mound-forming shrubs uniform and outwardly spreading plant habit; moderately vigorous growth habit and densely foliated. Individuals observed at about 2.5 years showed approximately 15 to 20 inches tall and 17 to 22 inches broad. A mature plant is 4-6 feet high and 4-5 feet wide. Crimson (greyed purple 187-A) on the upper and lower surfaces of the leaves; shades of green somewhat more evident on the upper surface, less so on the lower surfaces of the leaves. The crimson color is more intense on the new foliage and diminishes somewhat as the leaves age resulting in the older foliage having a deep crimson/green hue. Color differs significantly from standard 'Red Formosa' which has bright green foliage at all stages of maturity. Veins of 'Julonso', especially the midvein and secondary veins, on the underside of the leaves retain the crimson color as the leaves grow older. The cultivar has a semi-compact growth habitat. The cultivar has a red-purple flower color similar to that of Azalea 'Red Formosa'.

The following are the most outstanding and distinguishing characteristics of this new cultivar when grown under normal horticultural practices in Forest Hill, La.

1. The unique foliage coloration, color (mature leaves) greyed-green group, N189-A &-B 187-A on the upper leaf surface with more green apparent near the mid veins.
2. Easily propagated with semi-hardwood cuttings in late spring through the summer.
3. Fast growth rate under normal fertilization and moisture conditions.
4. Upright, dense and globose in nature.
5. Small semi-compact growth habitat, similar to the 'Crimson Queen'.
6. Makes a good container plant for under mid height or low height windows.
7. Useful in more confined landscape areas.
8. Groupings within landscape beds.

DESCRIPTION OF THE DRAWINGS

This new azalea variety is illustrated by the accompanying photographic prints in which.

Figure 1:
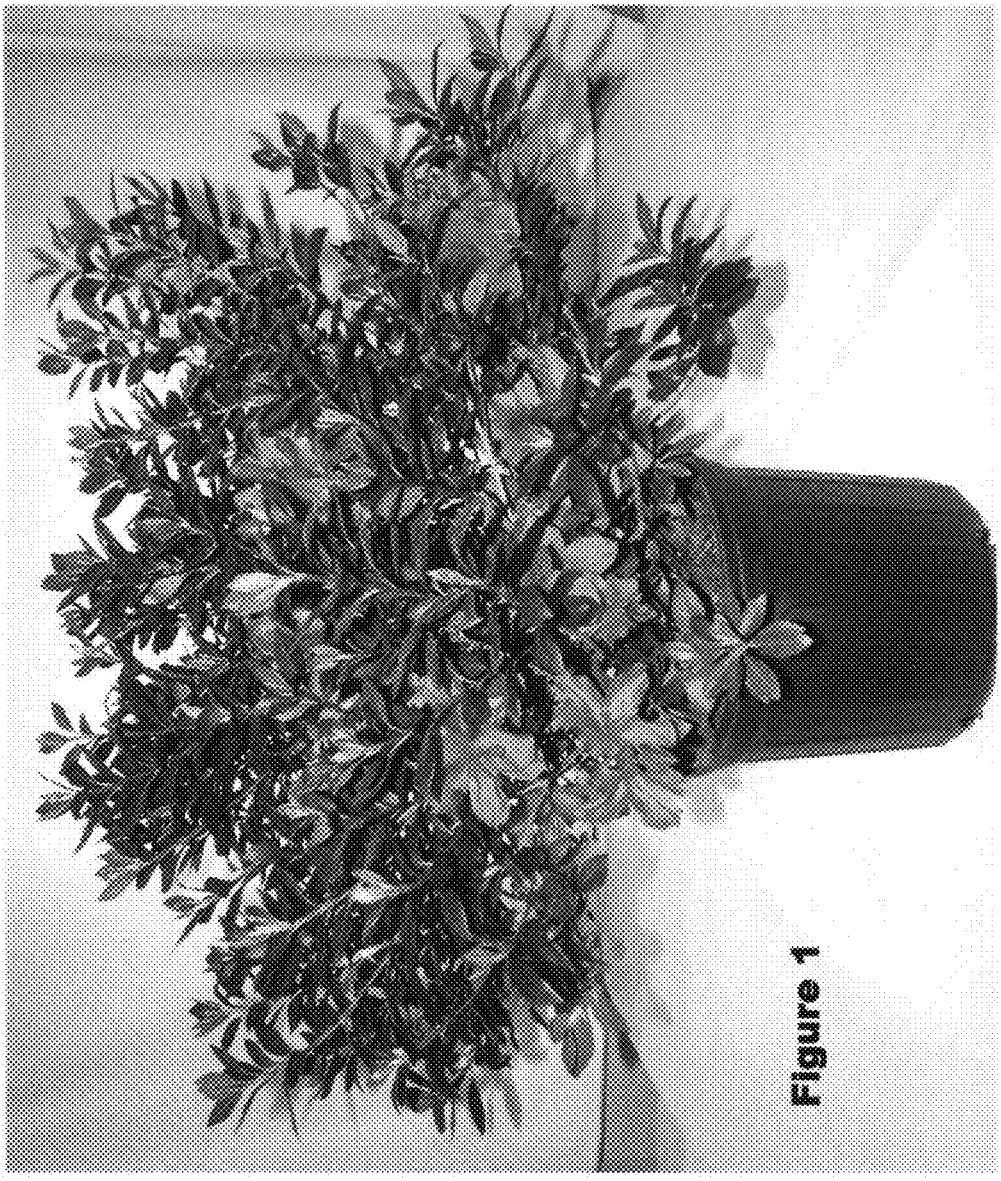
FIG. 1 is a view of the new azalea plant in three gallon, showing the plant at about 3 years of age.
Figure 2:
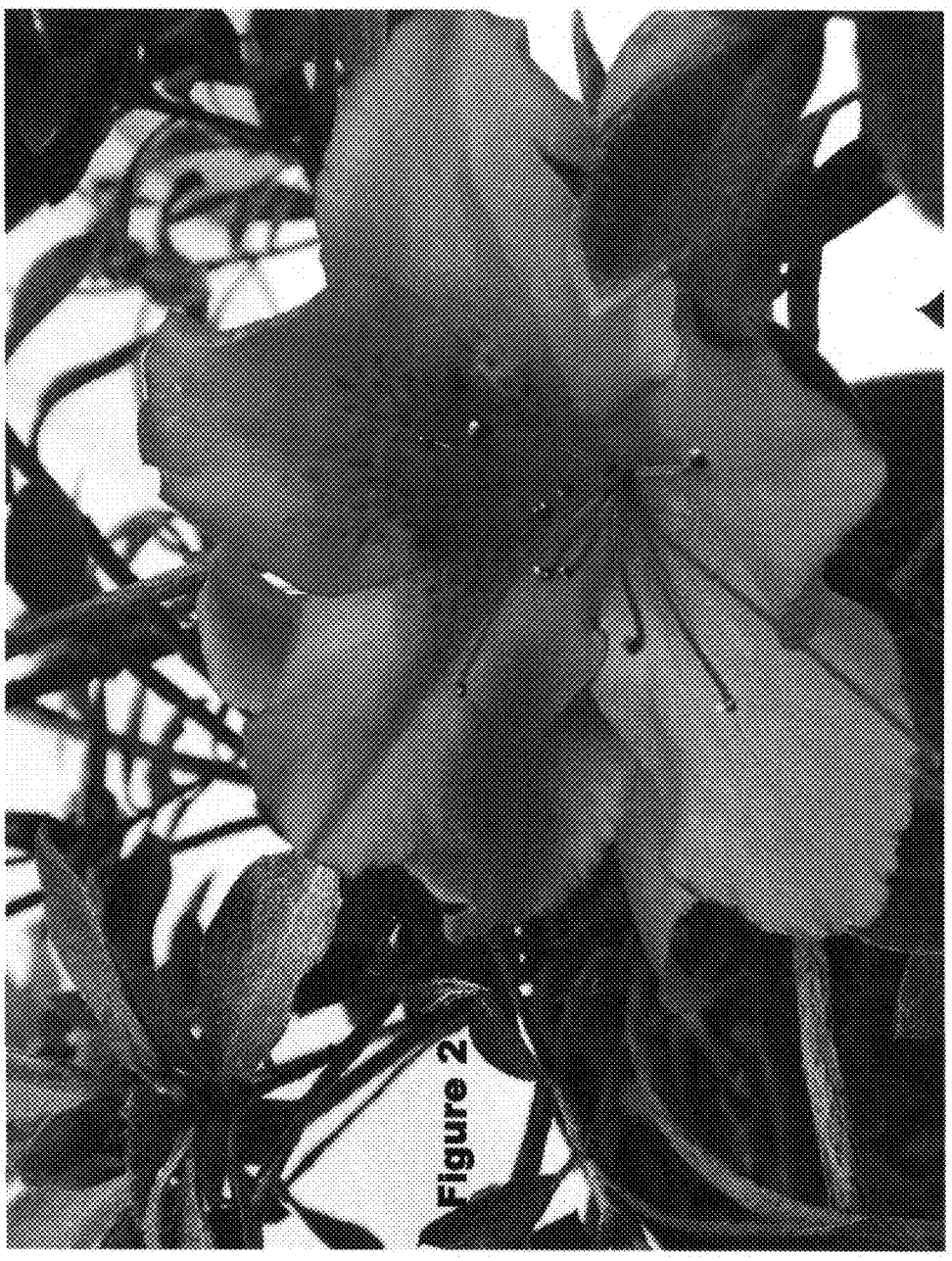
FIG. 2 is a close up view of the bloom of the new azalea.
Figure 3:
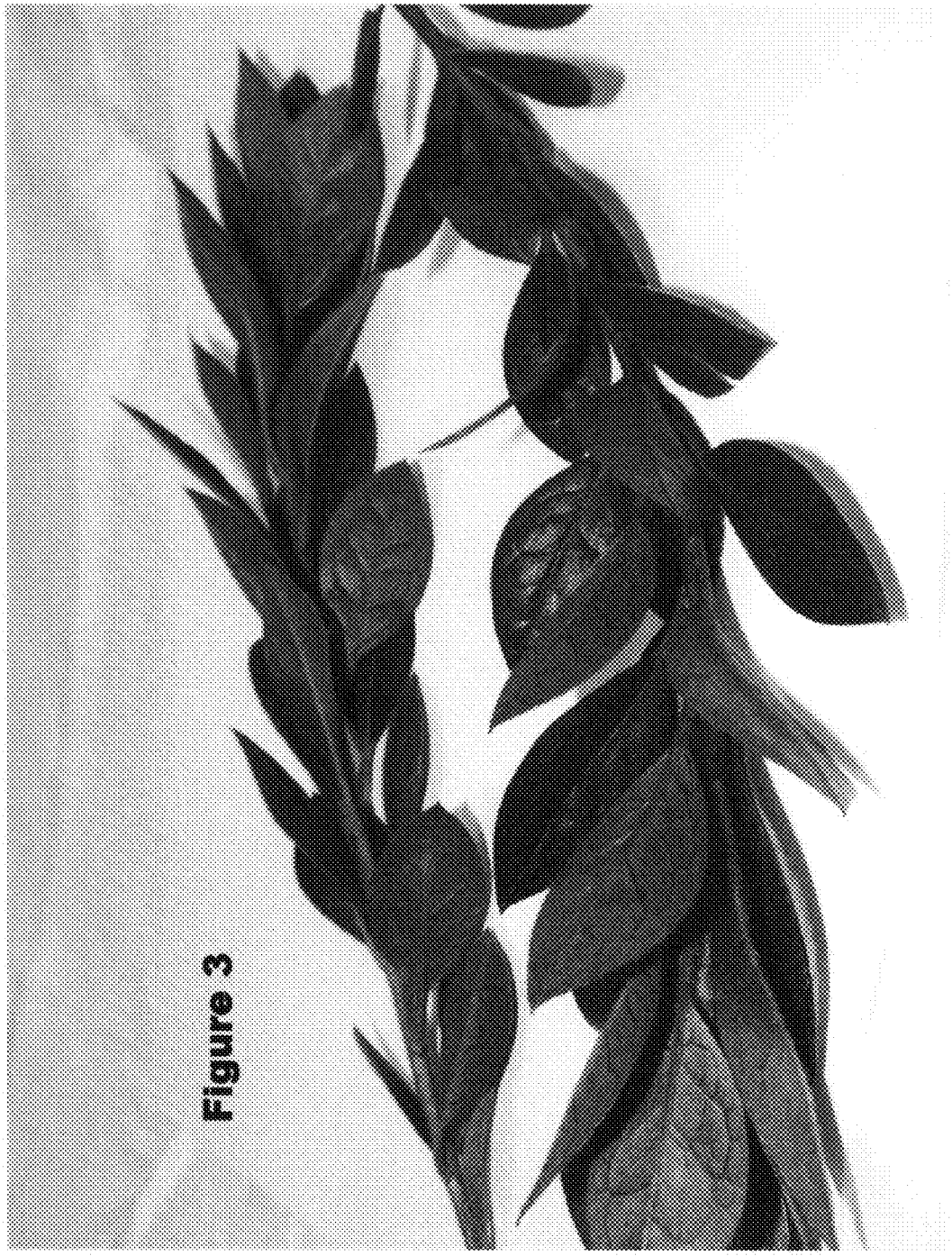
FIG. 3 shows a stem cuting of the new azalea showing the leaves top surface and underside surface.
Figure 4:
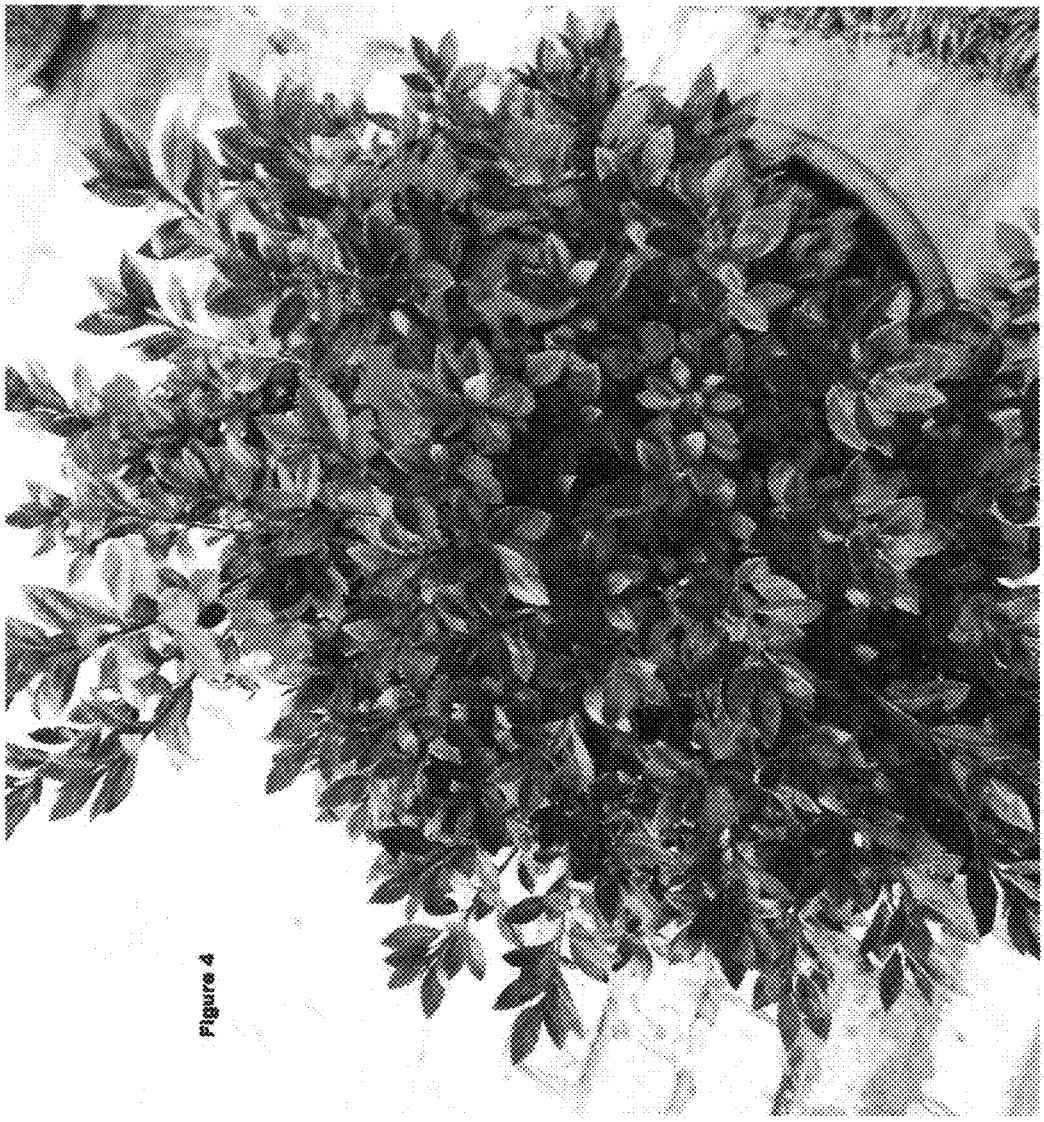
FIG. 4. is a top view of the plant shown in FIG. 1.

The colors shown are as true as is reasonably possible to obtain by conventional photographic procedures. The colors of the various plant parts are defined with reference to The Royal Horticultural Society Colour Chart (2001). Description of colors in ordinary terms are presented where appropriate for clarity in meaning. Colors in the photographs may appear different than actual colors due to light reflectance. Color values cited in the Botanical Description of the Plant accurately describe the actual colors of the new azalea.

DETAILED BOTANICAL DESCRIPTION

The following is a detailed description of the new variety of azalea based on observations made of plants grown in wholesale commercial production practices, in greenhouses, and in established landscape plantings in Forest Hill, La., and was compiled with the assistance of Dr. Lowell E. Urbatsch, Director of the LSU Herbarium, Louisiana State University.

BOTANICAL DESCRIPTION OF THE PLANT

Branching habit: Sympodial (branching without a main axis but with many, more or less, equal laterals). Seven to twelve stems are evident at or near ground level that branch and re-branch frequently and at close intervals. Branches are ascending or arcuate-ascending to upright. Branching may increase with maturity. Branch characteristics (on mature growth of the current season): branch length, 5-20 cm; branch diameter, 3-7 mm; internode length, 1-20 mm, branch strength is strong as is stem strength.

Characteristics of the plant in winter dormancy: During the winter, the plants are evergreen, i.e., the leaves remain on the stems. No signs of growth or flowering are evident during winter. Hardiness is expected to be the same as 'Red Formosa' cultivars, that is, hardy in zones 7-9.

A. BARK

Younger stems supporting flowers and newly formed leaves were rated as 185-A in the Grayed Purple Group; somewhat older ones were darker and rated 178-A Grayed Red Group; and the oldest of the woody stems were rated 201-A and -B, Grayed Group. These lower stems are rarely visible due to the compact leafy nature of the plants and they contribute little to its ornamental qualities.

B. INFLORESCENCE AND FLOWERS

Infloresence: Racemose; flowers appearing individually or in clusters of 2 or 3 each supported by pedicel (flower stalk) on leafy branches.

Flower buds: Flower buds just before anthesis are 5-angled and about 1.5 to 1.8 inches in length, similar to 'Red Formosa' cultivars. Corolla color of the flower bud is 64-B in the Red-Purple group. Rate of opening just after bud corolla becomes visible is about 2-3 days but rate is variable with temperature, sunlight, and possible other conditions. Corolla color becomes visible when bud is about 12 mm long and 8 mm wide. Flower bud shape is ovoid when viewed dosal-ventrally. When about 17 mm long and 10 mm wide the petals become visible and at about 4 cm long and 1.5-2 cm wide when the petals begin to open. In side view bud bulges slightly outward, inner surface is slightly concave. Overall, the bud has a somewhat falcate shape. As viewed from the top or in cross- section bud is slightly 5-lobed.

Flowers: Arranged singlely or mostly in groups of 2-3 flowers at stem terminus; flowers face outward and upward. The petals or corolla are 5 in number and basally fused forming a corolla tube about 1 to 1.4 inches in length and width; petal appearance is satiny; texture is smooth; petals are spatulate (obovate) with rounded apex and 2.2-3 inches long and width from lobe tip to lobe tip about 2.5 to 3.5 inches. The lobes measured from circa 1 to 1.25 inches long to about 1-1.3 inches wide. The corolla margins are minutely and regularly undulate or ruffled. Corollas compare favorably with 64-B in the Red-Purple group. Mature flowers range from appoximately 3-4 inches in diameter and about 2-3 inches in length.

Sepals: The whorl of sepals (collectively the calyx) outside of the corolla consists of a five lobed calyx, and measures approximately ¼ inch in length. Individually, the lobes are lanceolate and fused to one another only at their bases; they range from 7-10 mm long and 3-4 mm wide. They are yellowish green, approximately 141-C, in the Green Group of The R.H.S. Colour Chart and contribute little to the ornamental qualities of the flowers. Sepals are moderately pubescent abaxially (outer surface) and glabrous adaxially (inner surface are elliptic in shape and their margins are entire and the apex is acute. In zone 8, flowering season is approximately early April through early to mid May.

Reproductive organs: While insignificant in size, the filaments of stamens nevertheless are intensely colored (60-B, Red-Purple Group, fan 2); the anthers are much darker (N-77A, Purple Group, fan 2). They number 9-10 per flower in the specimens examined and have a filament length of from 1.2 to 2 inches (2.8-5.4 cm). The anthers are about 1/16 of an inch long (1.5-2 mm) and each releases pollen through a terminal pore. They are much darker than the filaments (N-77, Purple Group, fan 2). Gynoecium appears to consist of 5 fused carpels. The ovary is densely pubescent (sericeous) with the hairs obscuring ovary surface; hairs are shiny and closest to 60-C in color; ovary shape is ovoid and about 5 mm long. The style is about 4.5-5 cm long, 1.5 mm in diameter and near 59-B in color. The stigma is truncate (i.e., having a flat surface) to slightly convex and circular to slightly lobed in end view with a diameter of 1.5 mm.

Peduncle: Peduncle (i.e., the stalk supporting a cluster of flowers) length is from 15-20 mm long and about 2 mm in diameter; it is somewhat flexible and it provides strong support for the flower; it is moderately pubescent with uniseriate hairs; and near 60-B (fan 2) in color.

C. LEAVES

Arrangement: Leaves are alternate, that is one leaf per node. Leaves are spaced about 1/16 to about 1 inch apart along the stems (internode length). Leaf stalk (petiole) about 1/8 to 3/8 inches long.

Leaf shape: Leaves elliptic to oblanceolate in outline; apices acute to acuminate; bases cuneate to rounded. Margins are entire although generally bordered with ciliate hairs. Leaves are spaced about 1/4 to 3/24 inches apart along the stems. Leaf stalk (petiole) about 3/16 to 1/2 inches long.

Leaf size: 1/2 to 1 inch broad and 1 to 3 inches long including the petiole and 3/4 to 1.5 inches wide.

Leaf color: Crimson (185A-B, greyed-purple group), on the upper and lower surfaces; shades of green N189-A & -B, Grayed-Green Group, somewhat more evident on the upper surface more so toward the midvein and leaf base, less so marginally and on the lower surface. Intensity of color is greatest apically and marginally. The crimson color is more intense on the new foliage and diminishes somewhat as the leaves age resulting in the older foliage having a deep crimson/green hue. Color ratings for new growth leaves are 185-A & B, Grayed-Purple Group, while the older leaves approximate N189-A & -B, Grayed-Green Group, on the upper surface with more green apparent near the mid veins. Color differs significantly from standard 'Red Formosa' which has bright green foliage at all stages of maturity. Leaf Veins, especially the midvein and secondary veins, on the leaf undersides of the present cultivar retain the crimson color (185A-B, Greyed-Purple Group) with age. Veins on both leaf surfaces with age may become a greyed-orange color, 167 C-D, Greyed-Orange Group.

Indumentum: The indumentum or plant hairs (trichomes) are hirsute in nature, i.e. the individual hairs are uniseriate, slender, tapering at the tip and arising more or less perpendicular to the epidermis, and becoming somewhat flexuous slightly above the leaf surface. The hairs give the leaves and twigs a somewhat bristly texture. The same type of hairs are present on both the upper and lower leaf surfaces. In terms of density the indumentum is characterized as being moderately pubescent with the hairs being spaced about 1/32 inch (0.5 mm) apart. On the lower surface the hairs are somewhat more closely spaced along the veins and petioles. Indumentum on the stems is similar except for the hairs being somewhat more closely spaced than on the leaf blade surfaces. Its color typically is greyed-white, 156 B-C, Greyed-White Group, but may become similar to that of the midvein on older leaves, i.e. 167 C-D, Greyed-Orange Group.

D. OTHER

Fruit: Insignificant.

Petiole: Length 6-10 mm; diameter 1.5-3 mm wide, 1.5 mm thick; coloration: upper surface, 138-B Green Group with flecks of 59-A, Red-Purple Group; lower surface 59-A Red Purple Group with flecks of 138 B Green Group.

Fragrance: None evident.

Taste: Not relevant.

Disease resistances: Disease resistances. — No known Azalea diseases observed to date on plants grown under commercial conditions. Expected to be similar to 'Red Formosa' cultivars — resistant to flower and leaf gall, caused by *Exobasidium vaccinii* and root rot caused *Phytophthora cinnamomi*; susceptible to Lace bug and to petal blight caused by *Ovulinia azalea.*

Productivity of flowers and leaves: Similar to 'Red Formosa' cultivars, but flower production is slightly more profuse.

Vigor: Similar to 'Red Formosa' cultivars, hardy in zones 7-9.

The invention claimed is:

1. A new and distinct variety of azalea plant, substantially as shown and described.

* * * * *